United States Patent [19]
Jovanovic et al.

[11] Patent Number: 5,754,016
[45] Date of Patent: May 19, 1998

[54] METHOD OF CONTINUOUS CONTROL OF TIP VIBRATION IN A DENTAL SCALAR SYSTEM

[75] Inventors: Vidan Jovanovic, Flushings; Alfred E. Corbellini, Northport; Emery Rose, Astoria; George Warrin, North Merrick, all of N.Y.; Richard Paschke, Timonium, Md.

[73] Assignee: Dentsply Research & Development Corp, Milford, Del.

[21] Appl. No.: 715,663

[22] Filed: Sep. 18, 1996

[51] Int. Cl.⁶ .............................. A61C 1/07; H01L 41/08
[52] U.S. Cl. .............................. 318/118; 318/114
[58] Field of Search ........................ 318/114, 116, 318/118; 310/26; 433/118, 119; 601/2

[56] References Cited

U.S. PATENT DOCUMENTS

| | | | |
|---|---|---|---|
| 2,947,082 | 8/1960 | Epstein | 32/46 |
| 3,067,765 | 12/1962 | Aymar et al. | 137/376 |
| 3,414,000 | 12/1968 | Newton | 137/209 |
| 3,809,977 | 5/1974 | Balamuth et al. | 318/116 |
| 3,924,335 | 12/1975 | Balamuth et al. | 32/58 |
| 3,989,952 | 11/1976 | Hohmann | 307/38 |
| 3,994,069 | 11/1976 | Hohmann | 32/22 |
| 4,041,609 | 8/1977 | Bresnahan et al. | 32/22 |
| 4,184,092 | 1/1980 | Wieser | 310/316 |
| 4,194,289 | 3/1980 | Neri | 433/101 |
| 4,371,816 | 2/1983 | Wieser | 318/116 |
| 4,403,176 | 9/1983 | Cranston | 318/114 |
| 4,428,748 | 1/1984 | Peyman et al. | 604/22 |
| 4,479,098 | 10/1984 | Watson | 331/154 |
| 4,479,182 | 10/1984 | Beier | 364/413 |
| 4,523,911 | 6/1985 | Braetsch et al. | 433/101 |
| 4,571,681 | 2/1986 | Beier et al. | 364/413 |
| 4,587,958 | 5/1986 | Noguchi et al. | 128/24 |
| 4,676,750 | 6/1987 | Mason | 433/101 |
| 4,768,496 | 9/1988 | Kreizman et al. | 128/24 |
| 4,797,098 | 1/1989 | Kawata | 433/98 |
| 4,820,152 | 4/1989 | Warrin et al. | 433/86 |
| 4,878,841 | 11/1989 | McCulloch et al. | 433/72 |
| 4,965,532 | 10/1990 | Sakurai | 331/4 |

(List continued on next page.)

FOREIGN PATENT DOCUMENTS

| | | |
|---|---|---|
| 0 005 377 | 11/1979 | European Pat. Off. . |
| 0 229 003 | 7/1987 | European Pat. Off. . |
| 0 294 548 | 12/1988 | European Pat. Off. . |
| 0 328 352 | 8/1989 | European Pat. Off. . |
| 0 454 188 | 10/1991 | European Pat. Off. . |
| 0 525 539 | 2/1993 | European Pat. Off. . |
| 2338636 | 2/1975 | Germany . |
| 2459841 | 7/1976 | Germany . |
| 2530108 | 1/1977 | Germany . |
| 2710049 | 9/1978 | Germany . |
| 3136028 | 3/1983 | Germany . |
| 3817347 | 11/1989 | Germany . |
| 3900601 | 8/1990 | Germany . |
| 5-154164 | 6/1993 | Japan . |
| 6-1819933 | 7/1994 | Japan . |
| 1 457 913 | 2/1989 | U.S.S.R. . |
| 1 806 682 | 4/1993 | U.S.S.R. . |
| 1 433 978 | 4/1976 | United Kingdom . |
| 85/02106 | 5/1985 | WIPO . |
| WO 93 15 850 | 8/1993 | WIPO . |
| 94/10931 | 5/1994 | WIPO . |
| WO 95 20 374 | 8/1995 | WIPO . |

*Primary Examiner*—Steven L. Stephan
*Assistant Examiner*—Judson H. Jones
*Attorney, Agent, or Firm*—Dale R. Lovercheck; James B. Bieber

[57] ABSTRACT

The invention provides a method of operating a dental scalar system having a vibrating scaling tip by continuously monitoring the amplitude and frequency of vibration of the tip which provides scaling power to a tooth in a patient's mouth. The amplitude and frequency of vibration of the tip is continuously adjusted to maintain a substantially constant scaling power. Preferably, the insert is vibrated at its resonant frequency and the system provides a substantially constant tip motion while the user varies the applied pressure between the tip and the tooth.

13 Claims, 9 Drawing Sheets

OTHER PUBLICATIONS

| | | | |
|---|---|---|---|
| 5,026,387 | 6/1991 | Thomas | 606/169 |
| 5,033,238 | 7/1991 | Zubler | 51/165.74 |
| 5,059,122 | 10/1991 | Hetzel | 433/118 |
| 5,106,302 | 4/1992 | Farzin-Nia et al. | 433/215 |
| 5,130,619 | 7/1992 | Izuno | 318/116 |
| 5,139,509 | 8/1992 | Fischer et al. | 606/107 |
| 5,151,085 | 9/1992 | Sakurai et al. | 604/22 |
| 5,180,363 | 1/1993 | Idemoto et al. | 202/32 |
| 5,184,605 | 2/1993 | Grzeszykowski | 128/24 |
| 5,320,532 | 6/1994 | Farzin-Nia et al. | 433/215 |
| 5,406,503 | 4/1995 | Williams, Jr. et al. | 364/571.01 |
| 5,419,703 | 5/1995 | Warrin et al. | 433/216 |
| 5,421,829 | 6/1995 | Olichney et al. | 606/170 |

METHOD OF CONTINUOUS CONTROL OF TIP VIBRATION IN A DENTAL SCALAR SYSTEM

The invention relates to dental scaling systems. The dental scaling system and method of the invention provides continuous control of the frequency and amplitude of vibration of a dental scaling tip. Invention provides a dental scalar handpiece having a drive coil, buck coil and a feedback coil to control the amplitude and frequency of vibration of t he tip. The feedback coil generates an electronic feedback signal, that is proportional in amplitude and phase to both the electronic drive signal applied to the drive coil, and the magnetostrictive transducer characteristics. Variations in transducer amplitude and frequency of vibration for a particular transducer and for different transducers are minimized by continuously using a direct comparison of the feedback signal amplitude and feedback signal phase characteristic from the feedback coil in the handpiece to a user commanded input signal amplitude and the drive signal phase characteristic at the handpiece to continuously control tool tip vibration amplitude and frequency.

The feedback signal phase variation relative to the drive signal phase is used in conjunction with a phase lock loop circuit to maintain a nearly constant 90° phase shift between the two signals. This forces the frequency of operation to track the resonance of the magnetostrictive transducer. This provides substantially constant frequency of vibration under varying external conditions of use.

The feedback signal amplitude variation relative to a user commanded input signal is utilized by a feedback control circuit to set and maintain substantially constant, the amplitude of vibration of the magnetostrictive transducer. This provides substantially constant amplitude of vibration during varying external conditions. The tip (transducer) amplitude of vibration is controlled by pulse width modulating the power amplifier stage. This controls the drive signal duty cycle and the average power applied to the handpiece. Pulse width modulation is preferably implemented using a power amplifier having a Darlington device. Pulse width modulation facilitates using a power MOS-FET device as an alternative power amplifier implementation.

An alternate implementation for controlling the transducer's amplitude of vibration is by amplitude modulating the power amplifier stage thereby controlling the drive signal's amplitude and, as a result, the average power applied to the handpiece. The user commanded input signal is processed through a dual slope amplifier and amplitude conditioner that allows the feedback control system to operate using different magnetostrictive transducers (inserts). Typically, different insert types exhibit different feedback signal sensitivities, varying about two to one. The dual slope amplifier and amplitude conditioner adjusts, through the feedback control loop, the signal to the power amplifier minimizing these differences.

It is the object of the invention to provide a method of operating a dental scalar system having a vibrating scaling tip by continuously monitoring the amplitude and frequency of vibration of the tip which provides scaling power to a tooth in a patient's mouth.

Wieser in U.S. Pat. No. 4,371,816 discloses a control circuit for a ultrasonic dental sealer having one coil and without providing a user selectable range for the amplitude of vibration of the tip. Warrin et al in U.S. Pat. No. 4,820,152 disclosed a single multifunction handpiece for dental instruments.

Prior art dental sealers do not provide continuous control of tip vibration as is provided by the present invention.

Duty cycle as used herein refers to that portion of a recurring time interval during which power is applied and after which power is not applied. Increasing a duty cycle increases the length of time during which power is applied in one or more time intevals.

BRIEF DESCRIPTION OF THE INVENTION

The invention provides a method of operating a dental scalar system having a vibrating scaling tip by continuously monitoring the amplitude and frequency of vibration of the tip which provides scaling power to a tooth in a patient's mouth. The amplitude and frequency of vibration of the tip is continuously adjusted in response to external conditions to maintain a substantially constant tip motion. Preferably, the tip is vibrated at its resonant frequency and the system provides a substantially constant scaling action while the user varies the applied pressure of the tip against the tooth. Preferably, the dental sealer is excited (actuated) through the actions of a magnetostrictive transducer; a drive coil; a buck coil; and a feedback coil. Vibration of the magnetostrictive transducer induces a magnetostrictive characteristic signal in the feedback coil. Applying a drive signal to the drive coil causes the transducer to vibrate in response to the drive signal. The feedback signal is proportional in amplitude and phase to both the drive signal and the magnetostrictive characteristic signal. By comparing the feedback signal amplitude to a user commanded input signal amplitude, an amplitude comparison is provided. By controlling the drive signal amplitude in response to the amplitude comparison, and comparing the feedback signal phase with the drive signal phase, a phase comparison is provided and used to control the drive signal frequency in response to the phase comparison.

DETAILED DESCRIPTION OF A PREFERRED EMBODIMENT OF THE INVENTION

Figure 1A:
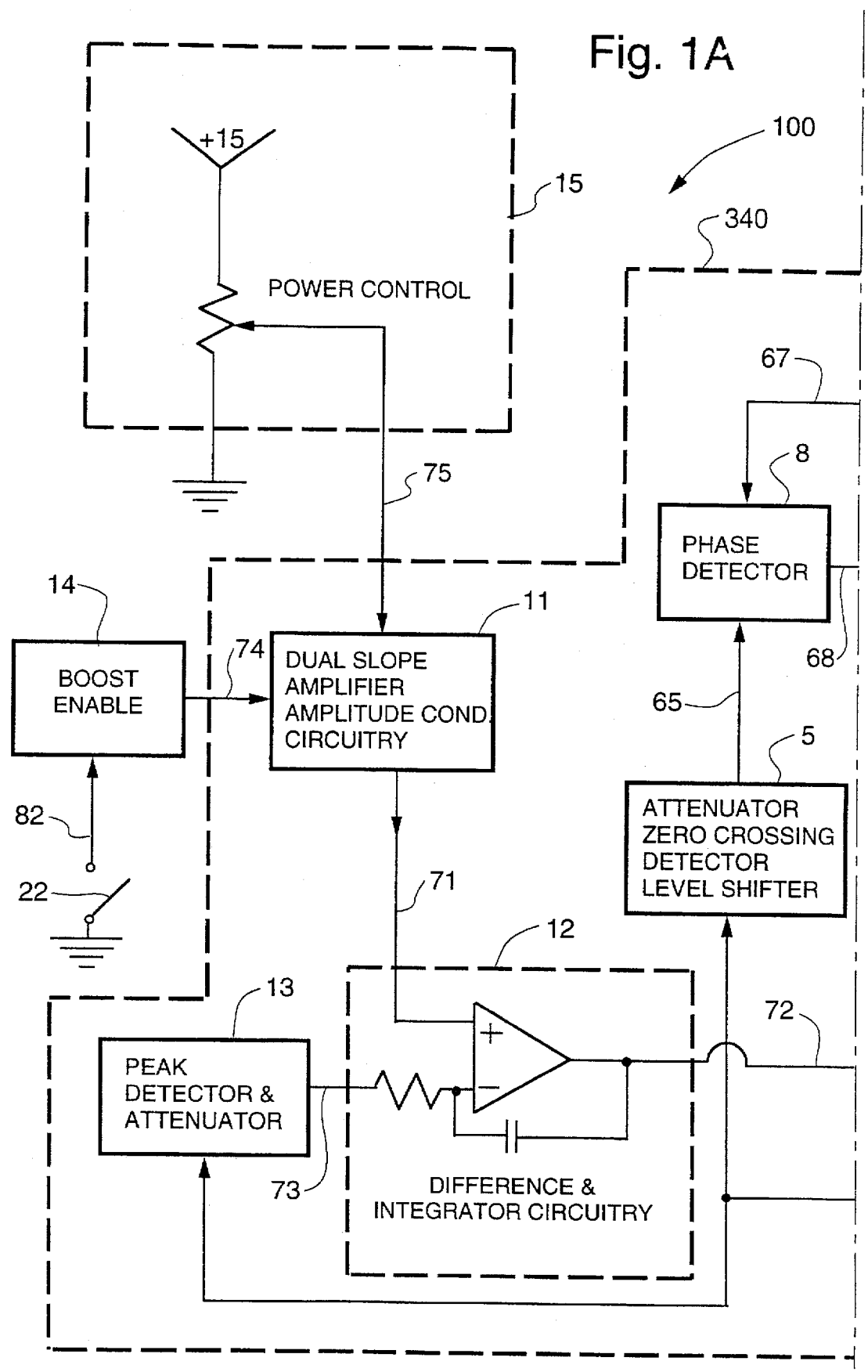
FIGS. 1a–1c are a schematic block diagram of a dental scalar system in accordance with the invention.
Figure 1B:
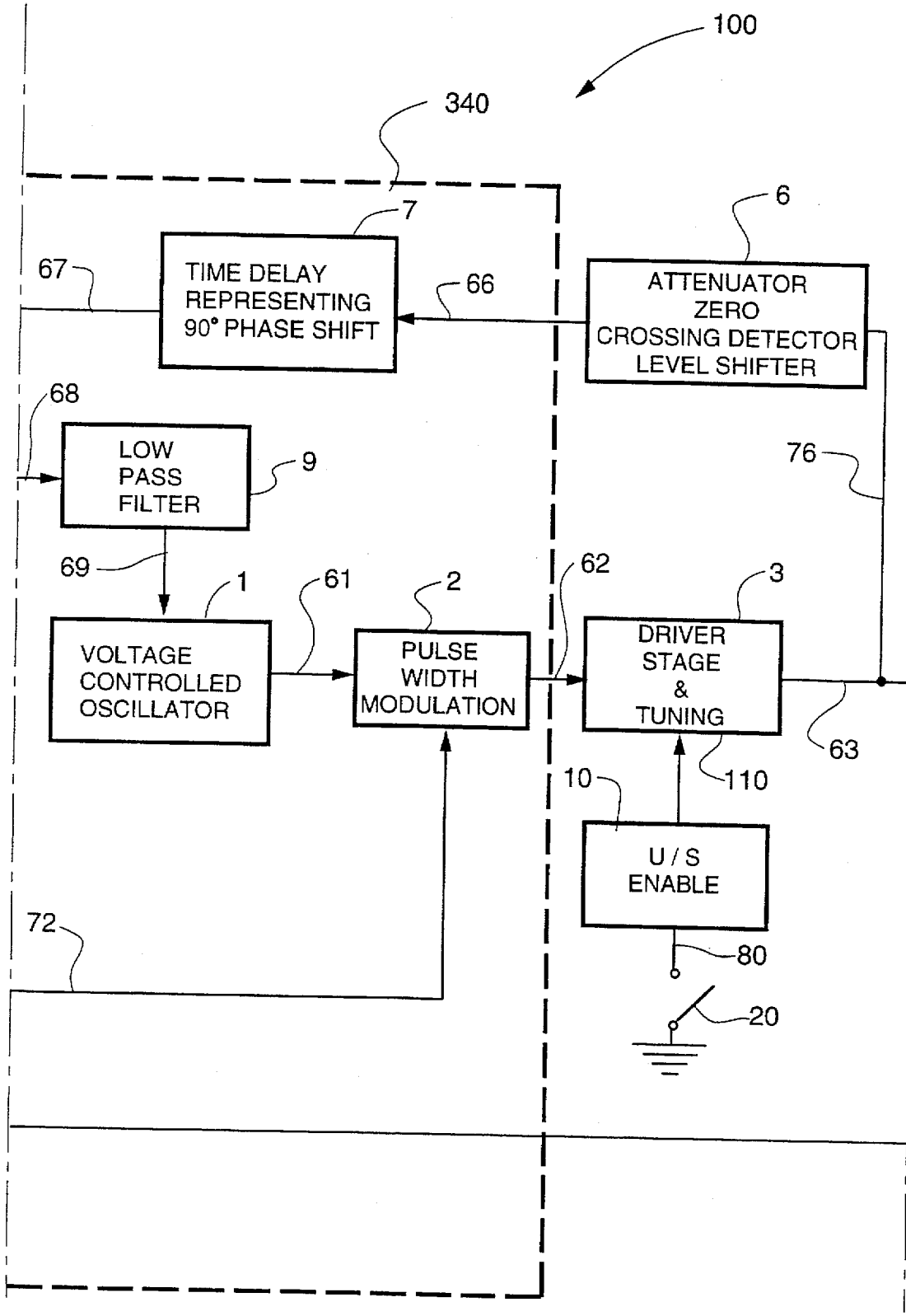
Figure 1C:
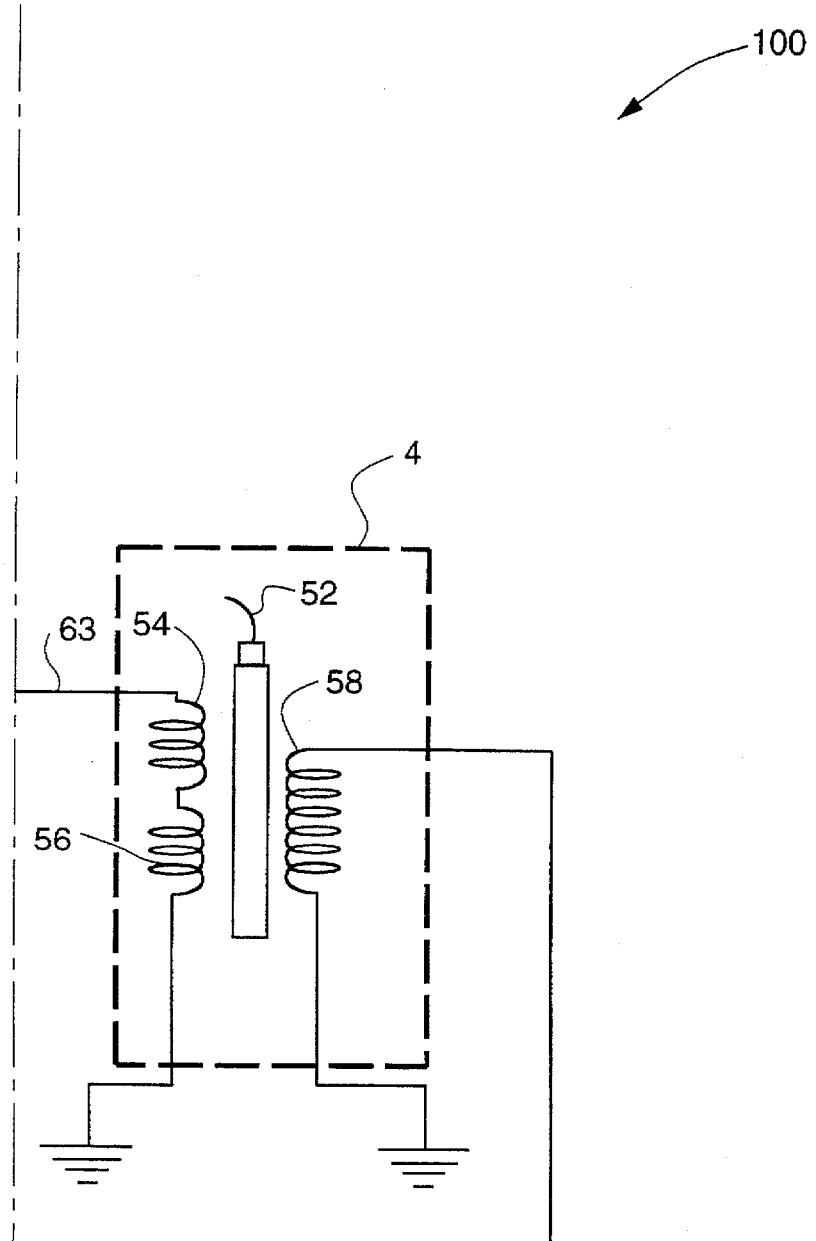

The invention is now described in reference to the FIGS. 1–4, which show a dental scaling system in accordance with the invention. With more particular reference to FIG. 1, is seen a dental scaling system 100. Dental scaling system 100 includes voltage controlled oscillator 1, pulse width modulator 2, drive stage and tuner 3, transducer 4, attenuator and zero crossing detectors 5 and 6, time delay 7, phase detector 8, filter 9, U/S enable 10, slope amplifier 11, integrator 12, peak detector and attenuator 13, boost enable 14 and variable resistance element 15.

Voltage controlled oscillator 1 is connected through electrical conductor 61 to pulse width modulator 2. Pulse width modulator 2 is connected through electrical conductor 62 to driver stage and tuning 3. Driver stage and tuning 3 is connected through electrical conductor 63 to transducer 4. Attenuator 5 is connected through electrical conductor 65 to phase detector 8. Attenuator 6 is connected through electrical conductor 66 to time delay 7. Time delay 7 is connected through electrical conductor 67 to phase detector 8. Phase detector 8 is connected through electrical conductor 68 to low pass filter 9. Low pass filter 9 is connected through electrical conductor 69 to voltage control oscillator 1. U/S enable 10 is connected through electrical conductor 110 to driver stage and tuning 3.

Dual slope amplifier and amplitude conditioner 11 is connected through electrical conductor 71 to difference and integrator 12. Difference and integrator 12 is connected through electrical conductor 72 to pulse width modulator 2. Peak detector and attenuator 13 is connected through electrical conductor 73 to difference and integrator 12. Boost enable 14 is connected through electrical conductor 74 to dual slope amplifier amplitude conditioner 11. A power control 15 is connected through electrical conductor 75 to dual slope amplifier amplitude conditioner 11. Foot switch 20 is connected through electrical conductor 80 to U/S enable 10. Foot switch 22 is connected through electrical conductor 82 to boost enable 14. Attenuator 6 is connected through electrical conductor 76 to transducer 4. Transducer 4 includes ultrasonic tip 52, and coils 54, 56, and 58.

Figure 2A:
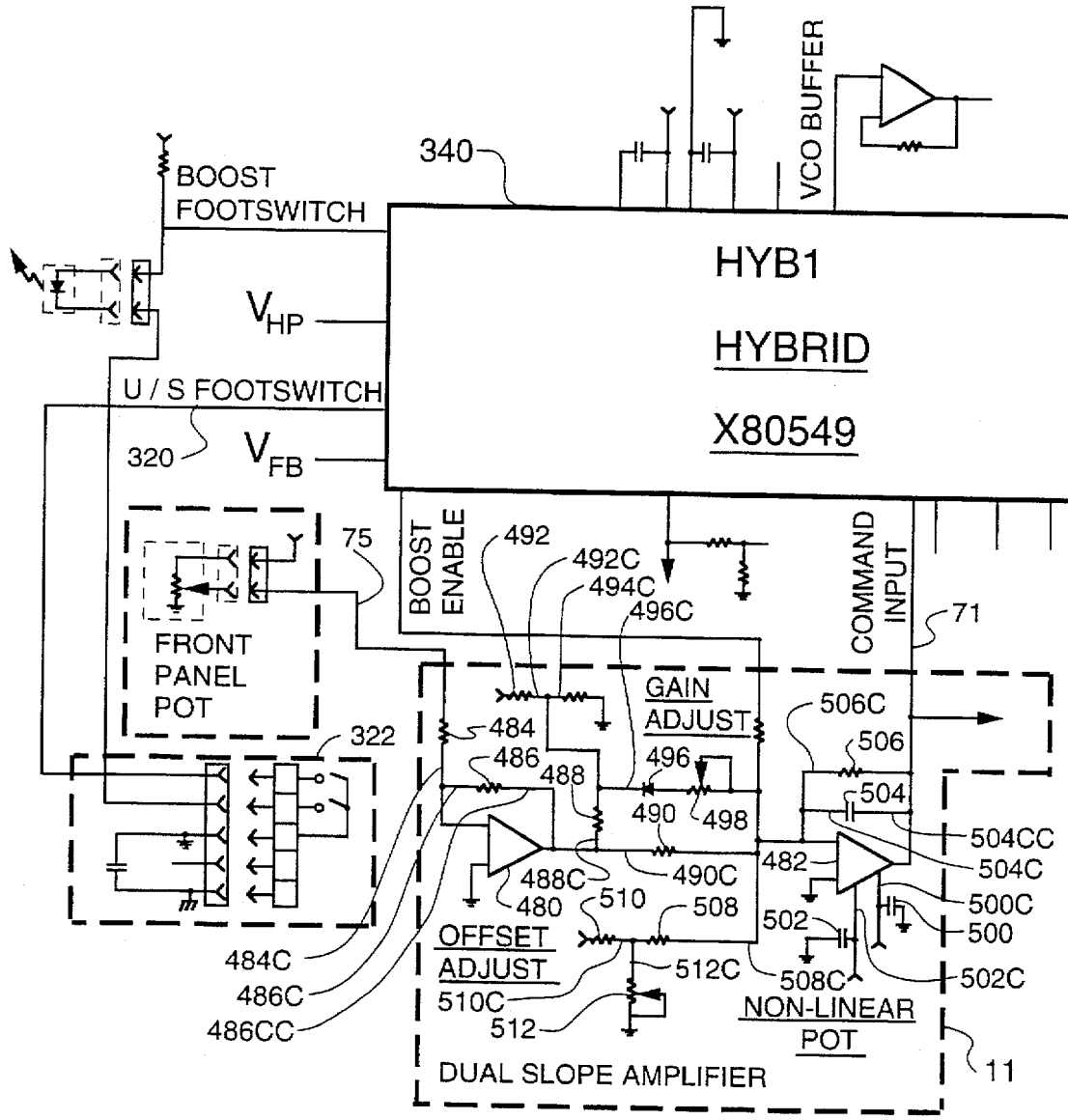
FIGS. 2a and 2b are a circuit diagram of the dental scalar system shown in FIG. 1.
Figure 2B:
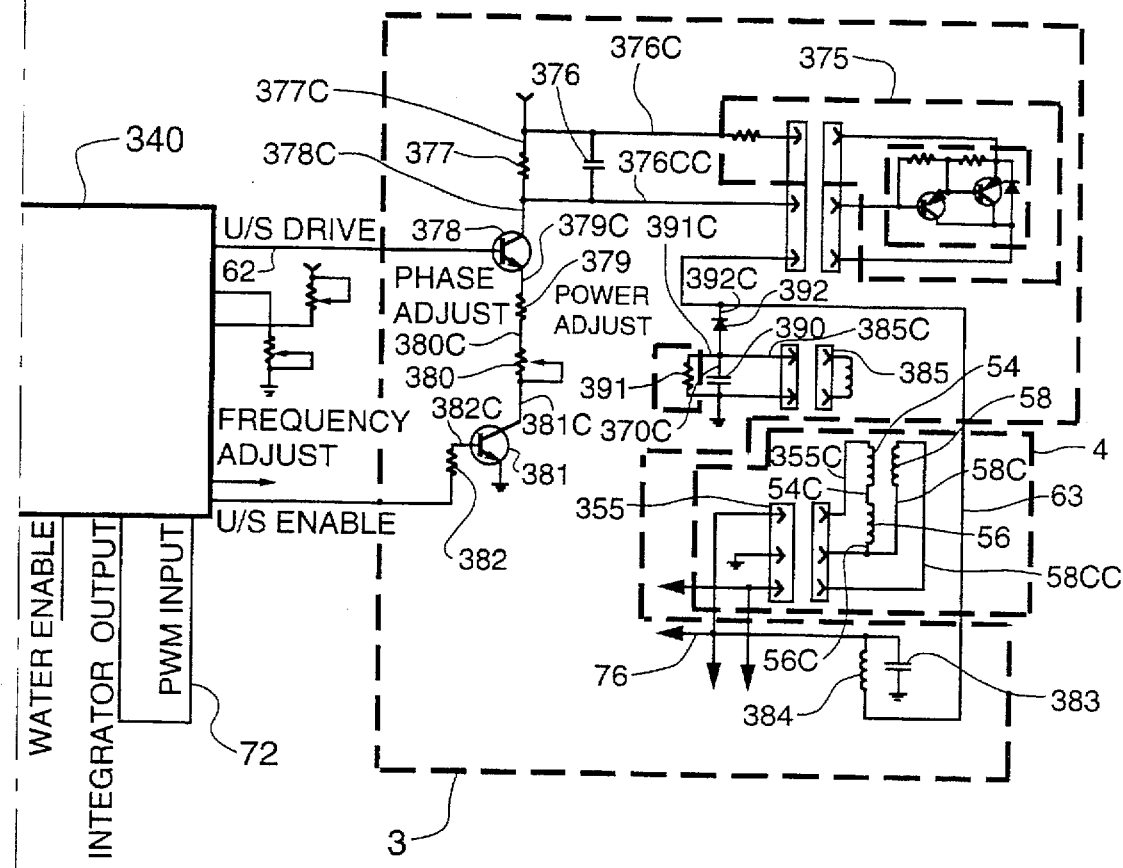
Figure 3A:
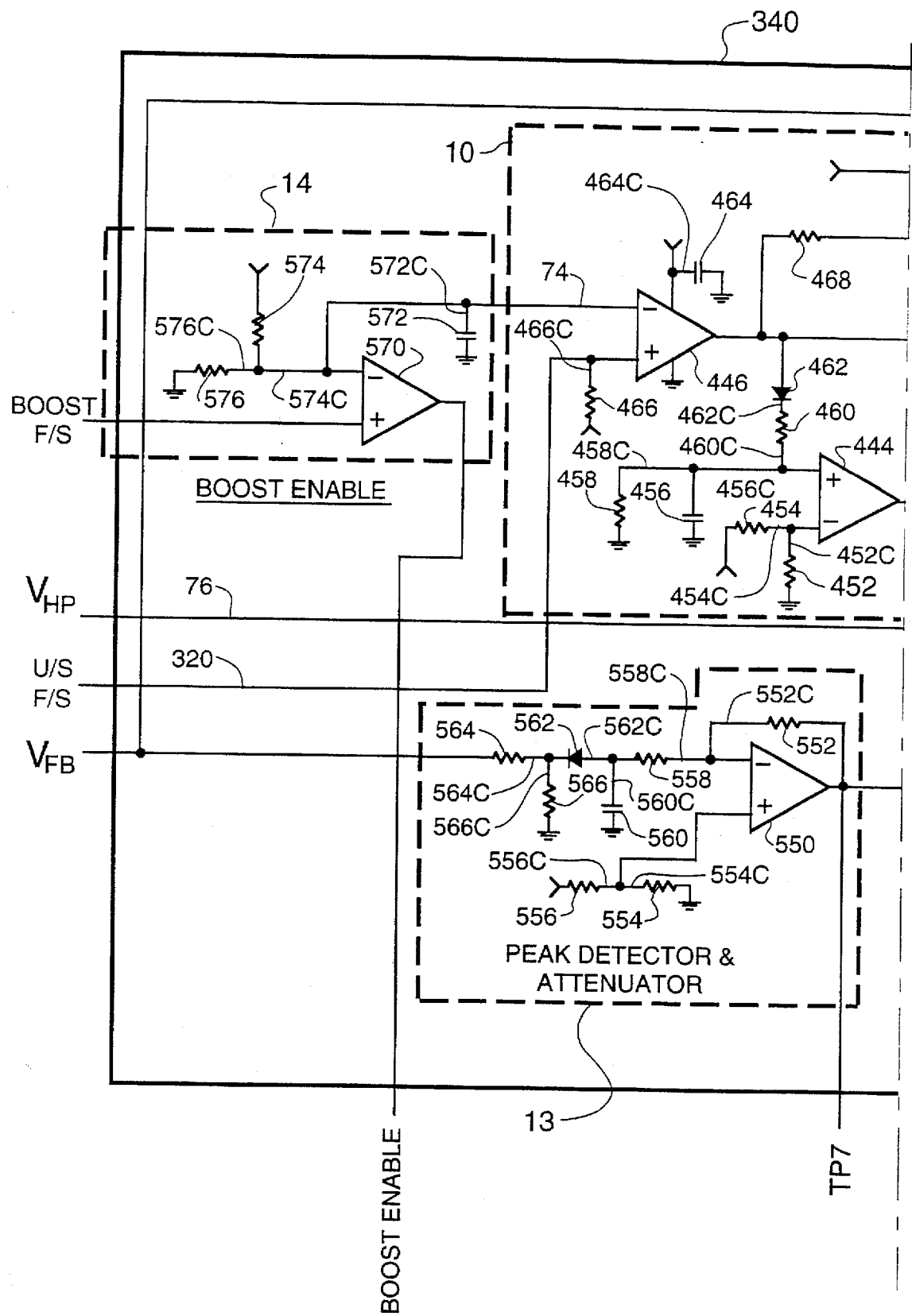
FIGS. 3a–3c are a circuit diagram of the portion of dental scalar system shown in FIG. 1.
Figure 3B:
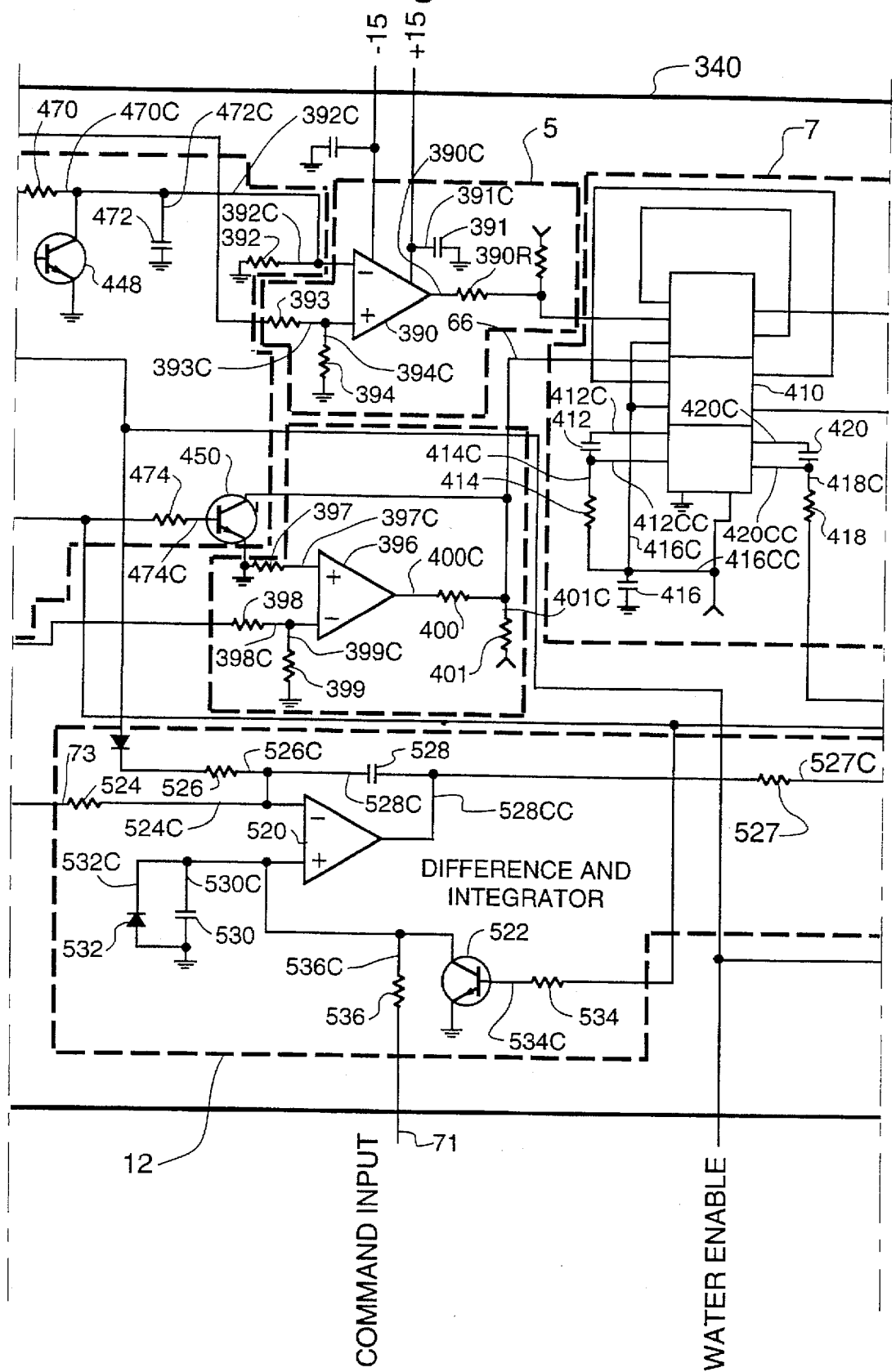
Figure 3C:
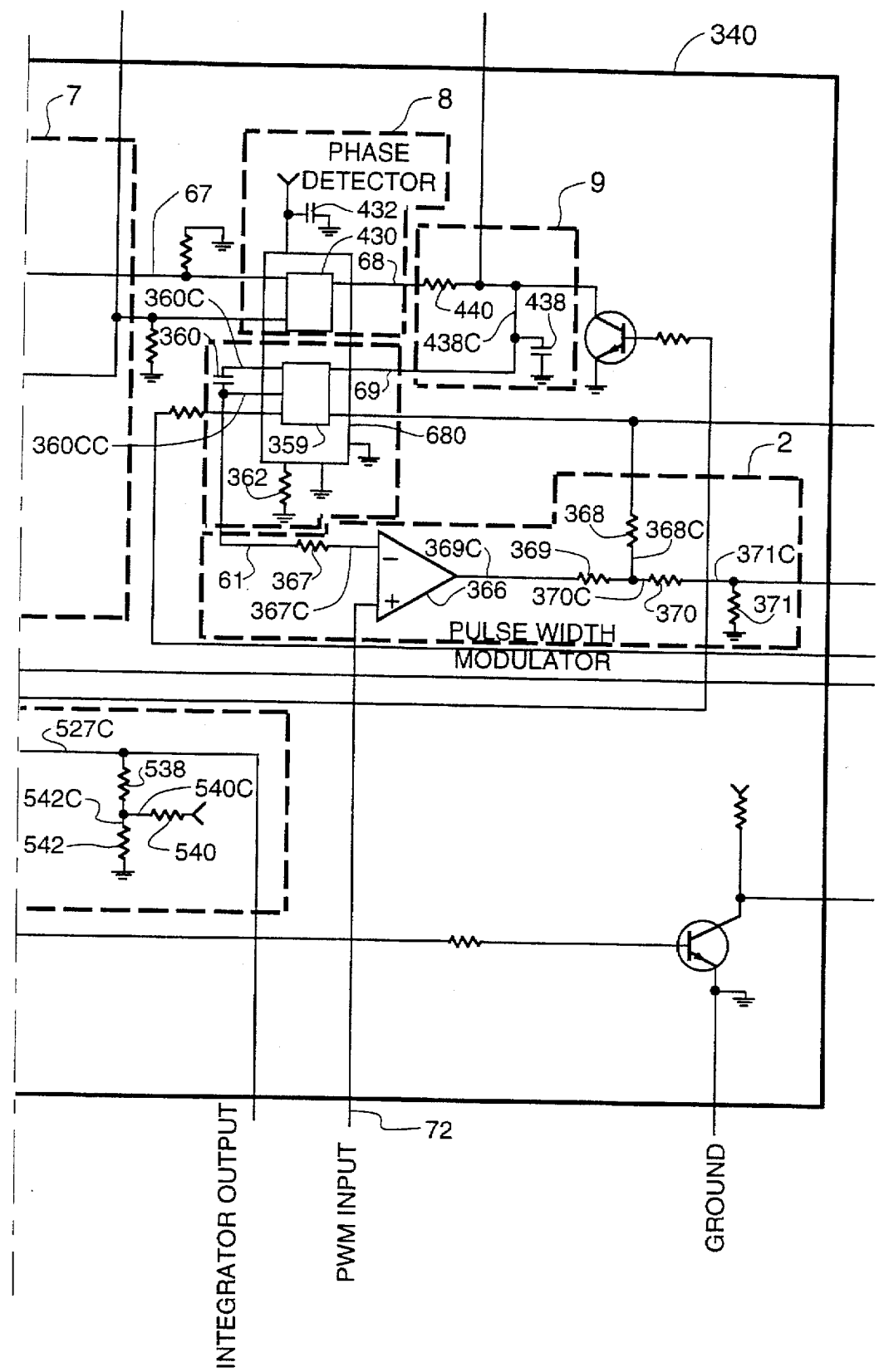

With m or e particular reference to FIGS. 2 and 3, it is seen that the voltage controlled oscillator 1 includes oscillator 359, capacitor 360 and resistor 362. Phase lock loop 680 (I.C.) is an integrated circuit (I.C.) device which includes oscillator 359 and phase comparator 430 as shown in FIG. 3. oscillator 359 is connected to capacitor 360 through electrical conductors 360C an 360CC. Phase lock loop integrated circuit 680 is connected by electrical conductors to capacitor 432 and resistor 362.

Pulse width modulator 2 includes comparator 366 and resistors 367, 368, 369, 370 and 371 as shown in FIG. 3. Comparator 366 is connected to resistors 367 and 369 through conductors 367C and 369C respectively. Resistor 369 is connected to resistors 368 and 307 through conductors 368C and 370C. Resistor 370 is connected to resistor 371 through electrical conductor 371C.

Driver stage and tuning 3 include sink and power amplifier 375, capacitor 376, resistor 377, transistor 378, resistor 379, variable resistor 380, transistor 381, resistor 382, capacitor 383, inductor 384, solenoid 385, capacitor 390, resistor 391 and diode 392 as shown in FIG. 2. Amplifier 375 is connected to capacitor 376, resistor 377, diode 372 and transistor 378 by electrical conductors 376C, 376CC, 377C, 378C and 392C as shown in FIG. 2. Transistor 378 is connected to resistor 379 through electrical conductor 379C. Resistor 379 is connected to variable resistor 380 through electrical conductor 380C. Variable conductor 380 is connected to transistor 381 through electrical conductor 381C. Transistor 381 is connected through electrical conductor 382C to resistor 382. Diode 392 is connected to capacitor 390 through electrical conductor 390C. Diode 392 is connected to resistor 391 to electrical 391C. Diode 392 is connected to solenoid 385 through electrical conductor 385C.

Handpiece 4 includes drive coil 54, connector 355, feed back coil 58 and bucking coil 56 as shown in FIG. 2. Coil 54 is connected to connector 355 through electrical conductor 355C. Coil 54 is connected to coil 56 through electrical conductor 354C. Coil 56 is connected to connector 355 through electrical conductor 56C. Coil 58 is connected to switch 355C through electrical conductor 58C and 58CC.

Attenuator and zero crossing detector 5 includes comparator 390, capacitor 391, resistor 390R, resistor 392, resistor 393 and resistor 394 as shown in FIG. 3. Comparator 390 is connected to capacitor 391, and resistors 390R, 392, 393 and 394 by electrical conductors 390C, 391C, 392C, 393C and 394C respectively as shown in FIG. 3.

Attenuator and zero crossing detector 6 includes comparator 396, resistor 397, resistor 398, resistor 399, resistor 400 and resistor 401 as shown in Figure 3. Comparator 396 is connected to resistors 397, 398, 399 and 400 by electrical conductors 397C, 398C, 399C and 400C respectively. Resistors 400 is connected to resistor 401 by electrical conductor 401C.

Time delay 7 includes non-retrigerable, mono-stable multivibrator I.C. device 410, capacitor 412, resistor 414, capacitor 416, capacitor 420 and resistor 418 as shown in FIG. 3. Multivibrator 410 is connected to capacitor 412 by electrical conductors 412C and 412CC. Multivibrator 410 is connected to resistor 414 through electrical conductor 414C. Multivibrator 410 is connected to capacitor 416 through electrical conductors 416C and 416CC. Multivibrator 410 is connected to capacitor 420 though electrical conductors 420C and 420CC. Capacitor 420 is connected to resistor 418 through electrical 418C.

Phase detector 8 includes comparator 430 and capacitor 432, as shown in FIG. 3.

Low pass filter 9 includes capacitor 438 and resistor 440, as shown in FIG. 3. Capacitor 438 is connected to resistor 440 by electrical conductor 438C.

U/S enable 10 includes amplifiers 444 and 446, transistors 448 and 450 as shown in FIG. 3. Amplifier 444 is connected to resistors 452, 454, 458 and 460 by electrical conductor lines 452C, 454C, 458C and 460C. Amplifier 444 is connected to capacitor 456 by electrical conductor line 456C. Resistor 460 is connected to diode 462 by electrical conductor 462C. Amplifier 446 is connected to capacitor 464 and resistor 466 by electrical conductors 464C and 466C. Transistor 448 is connected resistor 468, resistor 470 and capacitor 472 by electrical conductors 468C, 470C and 472C. Transistor 448 is connected to resistor 392 by electrical conductor 392C. Transistor 450 is connected to resistor 474 by electrical conductor 474C, as shown in FIG. 3.

Dual slope amplifier 11 includes amplifiers 480 and 482 as shown in FIG. 2. Amplifier 480 is connected to resistors 484, 486, 488 and 490 by electrical conductors 484C, 486C, 486CC, 488C and 490C. Resistor 488 is connected to resistors 492 and 494 and to diode 496 by electrical conductors 492C, 494C and 496C respectively. Diode 496 is connected to resistors 498 by electrical conductor 498C. Amplifier 482 is connected to capacitors 500, 502 and 504 and resistors 506 and 508 by electrical conductors 500C, 502C, 504C, 504CC, 506C and 508C respectively. Resistor 508 is connected to resistors 510 and 512 by electrical conductors 510C and 512C, as shown in FIG. 2.

Difference and integrator 12 includes amplifier 520 and transistor 522, as shown in FIG. 3. Amplifier 520 is connected to resistors 524 and 526 and capacitors 528 and 530 and diode 532 by electrical conductors 524C, 526C, 528C, 528CC, 530C and 532C respectively. Transistor 522 is connected to resistors 534 and 536 by electrical conductors 534C and 536C. Resistor 527 is connected to resistor 538 by electrical conductor 527C. Resistor 538 is connected to resistors 540 and 542 by electrical conductors 540C and 542C respectively.

Peak detector 13 includes amplifier 550 as shown in FIG. 3. Amplifier 550 is connected to resistor 552, 554, 556 and 558 by electrical conductors 552C, 554C, 556C and 558C. Resistor 558 is connected to capacitor 560 and diode 562 by electrical conductors 560C and 562C. Diode 562 is connected to resistors 564 and 566 by electrical conductors 564C and 566C, as shown in FIG. 3.

Boost enable 14 includes amplifier 570, as shown in FIG. 3. Amplifier 570 is connected to capacitor 572, resistor 574 and resistor 576 by electrical conductors 521C, 514C and 576C.

The scalar system of the invention includes two closed loops. One of the closed loops is configured to provide automatic tuning. That is, frequency of operation is automatically tuned to be at or near resonance of a particular insert.

The second loop automatically controls the output stroke level over different loading conditions. Transducer 4 includes drive coil winding 54, buck coil winding 56 and feedback coil winding 58. Transducer 4 also includes transducer tip 52.

The driving coil provides a field that causes the transducer to vibrate. The buck coil effectively cancels the driving field over that portion of the transducer where the feedback winding coil is positioned. The vibrating transducer generates its own magnetic field. The feedback winding picks up the magnetic field generated by the transducer vibration and converts it into the feedback voltage. Thus, the feedback voltage generated is directly portional to insert vibration.

Figure 4:
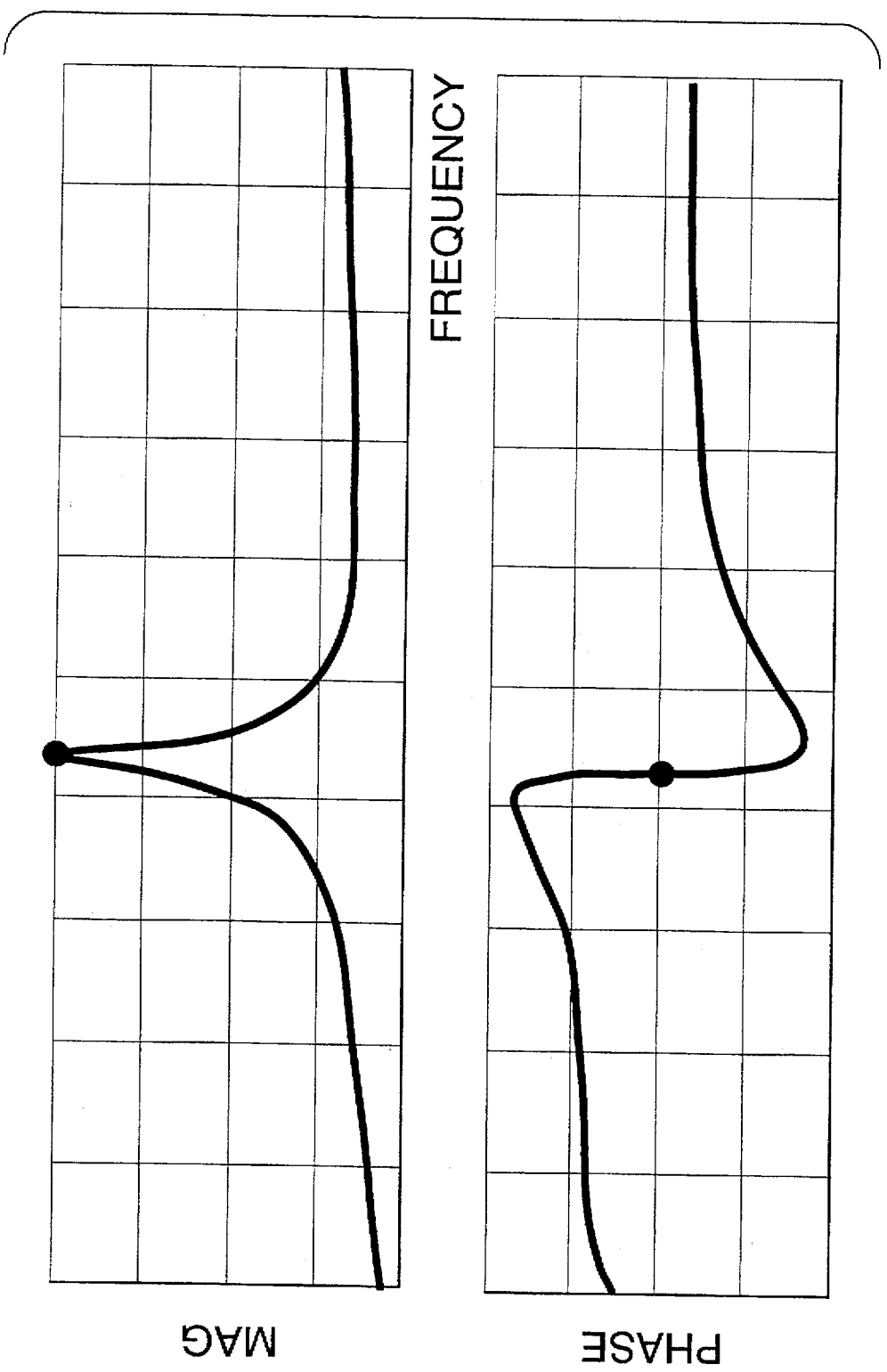
FIG. 4 shows a typical transfer function for feedback voltage and handpiece drive voltage.

FIG. 4 shows a typical transfer function for feedback voltage and handpiece drive voltage. At resonance, the ratio of feedback voltage to handpiece voltage is maximum. There is also a phase delay of about 90° between the two signals. This relationship is utilized in the invention to maintain the frequency of operation of the scaling tip at or near resonance.

Handpiece drive voltage is applied to attenuator 6 through line 76 from drive coil 54. Attenuator 6 is preferably a zero crossing detector (comparator) which in turn provides switching signal. This signal is delayed in time through time delay 7. Time delay 7 is preferably a non-retrigerable monostable multivibrator. This time delay corresponds to a 90° phase lag over the particular frequency range of the 30K insert. An output signal is transferred from time delay 7 through electrical conductor 67 to phase detector 8. Phase detector 8 receives an input signal from attenuator 5 through line 65. Attenuator 5 receives a signal from feedback coil 58 through electrical conductor 130. Low pass filter 9 receives a signal from phase detector 8 through electrical conductor 68. Preferably Low pass filter 9 is a resistance capacitance network which generates a direct current voltage that is proportional to the phase difference between the two inputs. This voltage is then applied to the voltage controlled oscillator 1. The voltage controlled oscillator 1 generates a frequency proportional to the DC voltage input that drives the pulse width modulation circuit 2. Pulse width modulator 2 sends an output signal through electrical conductor 62 to driver stage and tuning network 3. Driver stage and tuning network 3 transmits the handpiece voltage drive signal to the drive coil 54 through electrical conductor 63.

Phase Lock is obtained by initially running the voltage controlled oscillator 1 below the resonant frequency of any insert. Typically operating the voltage oscillator 1 below a frequency of 25 kHz with the low pass filter 9 providing zero volts DC is sufficient to cover the resonant frequency range of applicable inserts.

After enabling the system through U/S enable 10, by depressing foot switch position 1, the initial frequency of 25 kHz is applied to the transducer. The generated handpiece voltage drive signal and, in turn, the feedback voltage signal drive the phase detector 8. The phase detector generates an error voltage which charges the low pass filter to a new D.C. level which is greater than zero volts. In turn, the voltage controlled oscillator starts to increase in frequency. This change in frequency will stop only when the phase detector reaches 0° phase shift between its two inputs. But because of our time delay, which represents a 90° phase shift in the handpiece drive signal, 0° phase shift for phase detector inputs will happen when feedback voltage and handpiece voltage drive signals have 90° phase shift between them. But, from FIG. 4 we see that this 90° phase shift between the two signals occurs at the resonance condition.

Utilizing the handpiece voltage drive and the feedback voltage signal directly from the transducer provides unexpectedly superior maintenance of resonance conditions. The invention provides extremely low stroke operation for subgingival applications while maintaining resonant frequency. It is unnecessary to manually detune the system to obtain very low strokes.

The handpiece has a drive coil, a buck coil and a feedback coil for the acceptance of and generation of electrical signals utilized in conjunction with a magnetostrictive transducer and associated control circuitry. The feedback coil generates an electronic signal, the feedback signal, that is proportional in amplitude and phase to both the electronic signal applied to the drive coil, the drive signal, and the magnetostrictive transducer characteristics. Affects of variations in transducer characteristics due to external conditions are minimized since a direct comparison of feedback signal amplitude and phase characteristics at the handpiece are utilized in the control circuitry.

The feedback signal phase variation relative to the drive signal phase is used in conjunction with a phase lock loop circuit to maintain a nearly constant 90° phase shift between the two signals forcing the frequency of operation to track the resonance of the magnetostrictive transducer for optimum vibration under varying external conditions.

The feedback signal amplitude variation relative to a user commanded input signal is used in conjunction with a feedback control circuit to set, and continuously maintain nearly constant, the amplitude of vibration of the magnetostrictive transducer for optimum performance under varying external conditions. The transducer's amplitude of vibration is controlled by pulse-width modulating the power amplifier stage thereby controlling the drive signal's duty cycle and, as a result, the average power applied to the handpiece. Pulse-width modulation is preferably implemented in the power amplifier utilizing a power MOS-FET device or a bipolar Darlington device.

An alternate implementation for continuously controlling the transducer's amplitude of vibration is by amplitude modulating the power amplifier stage thereby controlling the drive signal's amplitude and, as a result, the average power applied to the handpiece. The use commanded input signal is processed through a dual-slope amplifier and amplitude conditioner that allows the feedback control system to operate properly with a range of magnetostrictive transducers possessing feedback signal sensitivities on the order of two to one. The dual-slope amplifier and amplitude conditioner ameliorates the difference between transducer types to provide better overall resolution and close upper end performance.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A continuously controlled dental scaling method comprising:

providing a dental scalar having
a magnetostrictive transducer having a tip;

a drive coil;

a buck coil; and a feedback coil, said magnetostrictive transducer having a magnetostrictive characteristic signal, applying a drive signal to said drive coil in response to a user commanded input signal, said drive signal inducing a feedback signal and a magnetostrictive characteristic signal in response to said drive signal, said feedback signal being proportional in amplitude and phase to said drive signal, said magnetostrictive characteristic signal being proportional in amplitude and phase to said drive signal, comparing said feedback signal amplitude to said user commanded input signal amplitude to provide an amplitude comparison, controlling said drive signal amplitude in response to said amplitude comparison, comparing said feedback signal phase with said drive signal phase, to provide a phase comparison, controlling said drive signal frequency in response to said phase comparison.

2. The method of claim 1 wherein said feedback signal has a phase variation relative to said drive signal of between 85° and 95° of phase shift at resonance, said feedback signal phase variation being maintained by a phase locked loop, whereby the frequency of the vibration of said magnetostrictive transducer is maintained substantially at the resonant frequency of said magnetostrictive transducer.

3. The method of claim 1 wherein said feedback signal has an amplitude variation when compared to a controlling input signal and said amplitude variation is fed to a feedback control circuit.

4. The method of claim 1 wherein said dental sealer further comprises a power amplifier.

5. The method of claim 4 wherein said dental sealer further comprises a pulse width modulator for pulse width modulating the power amplifier signal from said power amplifier within a closed loop circuit, said pulse width modulator being connected to conduct said pulse width modified signal to said drive coil.

6. The method of claim 5 wherein said pulse width modulator comprises a power MOS-FET device.

7. The method of claim 5 wherein said pulse width modulator comprises amplitude modulating a bipolar Darlington device.

8. The method of claim 1 wherein said dental sealer further comprises a dual slope amplifier and amplitude conditioner.

9. The method of claim 1 further comprising applying a varying load force to the insert tip that affects tip motion and the magnetostrictive characteristic signal, said change in magnetostrictive characteristic signal being reflected in a proportional change in the feedback signal, said change in feedback signal being reflected in a proportional change in the drive signal that acts in a direction to cancel said change in tip motion.

10. The method of claim 1 wherein said dental sealer further comprises a footswitch, said footswitch having a first and second position contacts.

11. The method of claim 10 wherein said second position provides a momentary boost in amplitude of vibration without requiring operator to leave operating field physically or visually.

12. The method of claim 1 wherein said dental sealer comprises and increases range of amplitude of vibration, particularly very low levels, without tuning off resonance.

13. The method of claim 1 wherein said magnetostrictive characteristic signal being proportional in amplitude and phase to external forces exerted on said tip.

* * * * *